(12) United States Patent
Duret et al.

(10) Patent No.: US 11,759,091 B2
(45) Date of Patent: Sep. 19, 2023

(54) DEVICE FOR VISUALIZING AN INTERIOR OF A PATIENT'S MOUTH

(71) Applicants: François Duret, Fleury d'Aude (FR); Olivier Querbes, Esqualquens (FR); Véronique Querbes-Duret, Esqualquens (FR)

(72) Inventors: François Duret, Fleury d'Aude (FR); Olivier Querbes, Esqualquens (FR); Véronique Querbes-Duret, Esqualquens (FR)

(73) Assignee: CONDOR SAS, Fleury d'Aude (FR)

( * ) Notice: Subject to any disclaimer, the term of this patent is extended or adjusted under 35 U.S.C. 154(b) by 905 days.

(21) Appl. No.: 14/589,697

(22) Filed: Jan. 5, 2015

(65) Prior Publication Data

US 2015/0350517 A1  Dec. 3, 2015

(30) Foreign Application Priority Data

May 27, 2014 (FR) .................................. 14 54774
Nov. 27, 2014 (FR) .................................. 14 61539

(51) Int. Cl.
  *H04N 5/232*  (2006.01)
  *A61B 1/00*  (2006.01)
  *G06T 7/00*  (2017.01)
  *A61B 1/05*  (2006.01)
  *A61B 1/24*  (2006.01)
  (Continued)

(52) U.S. Cl.
  CPC ...... *A61B 1/00009* (2013.01); *A61B 1/00045* (2013.01); *A61B 1/00048* (2013.01); *A61B 1/05* (2013.01); *A61B 1/24* (2013.01); *A61C 9/0053* (2013.01); *G02B 27/017* (2013.01); *G02B 27/0176* (2013.01); *G06T 7/0014* (2013.01); *G06T 19/006* (2013.01); *H04N 23/56* (2023.01); *H04N 23/66* (2023.01); *G02B 2027/014* (2013.01); *G02B 2027/0138* (2013.01); *G02B 2027/0141* (2013.01); *G02B 2027/0178* (2013.01); *G06T 2207/10068* (2013.01); *G06T 2207/10141* (2013.01);
  (Continued)

(58) Field of Classification Search
  CPC .............. H04N 5/23203; H04N 5/2256; G06T 7/0014; G06T 2207/10068; A61B 1/24; A61B 1/05; A61B 1/00048
  See application file for complete search history.

(56) References Cited

U.S. PATENT DOCUMENTS

6,344,853 B1 * 2/2002 Knight ................. G06Q 10/087
                                                                    345/629
7,909,606 B2 * 3/2011 Marcello .............. A61C 9/0046
                                                                    433/215
(Continued)

*Primary Examiner* — Shawn S An
(74) *Attorney, Agent, or Firm* — Craft Chu PLLC; Andrew W. Chu (57) ABSTRACT

The device for visualizing the interior of a patient's mouth, includes a camera for taking an optical imprint of organs arranged in the mouth. The device includes augmented reality glasses having an optical glass through which a user of the glasses can see the inside of the mouth, and a visualization camera taking an image of what the user sees through the optical glass. First images corresponding to those taken by the visualization camera are correlated with second images corresponding to those taken by the camera for taking an optical imprint, whereby the second images can be projected onto the optical glass.

14 Claims, 8 Drawing Sheets

(51) Int. Cl.
*G06T 19/00* (2011.01)
*G02B 27/01* (2006.01)
*A61C 9/00* (2006.01)
*H04N 23/56* (2023.01)
*H04N 23/66* (2023.01)

(52) U.S. Cl.
CPC ............ *G06T 2207/20221* (2013.01); *G06T 2207/30036* (2013.01); *G06T 2210/41* (2013.01)

(56) References Cited

U.S. PATENT DOCUMENTS

| | | | |
|---|---|---|---|
| 9,197,864 B1* | 11/2015 | Starner | H04N 5/23222 |
| 2004/0070600 A1* | 4/2004 | Morrisroe | G06F 17/3089 |
| | | | 715/738 |
| 2013/0108981 A1* | 5/2013 | Duret | A61B 1/24 |
| | | | 433/30 |
| 2014/0055563 A1* | 2/2014 | Jessop | A61B 1/00188 |
| | | | 348/45 |
| 2014/0378762 A1* | 12/2014 | Hirabayashi | A61B 1/045 |
| | | | 600/109 |
| 2017/0312064 A1* | 11/2017 | Jaisson | A61C 13/34 |

* cited by examiner

DEVICE FOR VISUALIZING AN INTERIOR OF A PATIENT'S MOUTH

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to a device for visualizing the interior of a patient's mouth. It also relates to an intraoral measuring device.

2. Description of Related Art Including Information Disclosed Under 37 CFR 1.97 and 37 CFR 1.98

A device for visualizing the interior of a patient's mouth is known, which comprises an intraoral camera adapted for taking an optical imprint of a patient's mouth and a remote display screen permitting a user of the device to visualize the images taken by the intraoral camera. Such a device is used namely for the production of dental prostheses.

The drawback of such a device is that the user must constantly watch the remote screen on which are displayed images corresponding to those taken by the intraoral camera (either the images taken by the camera or images proceeding from a data processing for modeling from the images taken by the camera), which thus obliges him to take his eyes off the patient's mouth and impedes him from having a correspondence between the patient's mouth, where he carries out his work, and what is displayed on the screen (for example, the actual result of his work, or the representation of what his work should finally be).

Thus, when taking an optical imprint, the user must manually scan with the intraoral camera the entire mouth area involved by the taking of the imprint. He must thus follow the evolution of the taking of an imprint, which can be displayed on the remote screen and therefore take his eyes off the patient's mouth.

The change in watching direction can result into adverse, inaccurate and uncontrolled movements of the user's hands, which may cause an injury to the patient (inside or outside the mouth). This drawback can be more important if the user takes a dynamic three-dimensional optical imprint.

Furthermore, the change in watching direction is also very tiring, the more when the rhythm of this movement is very high, for example more than twenty eye movements back and forth per minute.

In the case where the visualizing device uses a structured active light projector, the correlation of the modeled actual images with information from the augmented reality is very difficult because of the projection of masks (point, line, grid) on the teeth or the gum.

In addition, if indications in addition to the images taken by the intraoral camera are also displayed on the screen, the user must then make the additional effort of mentally transposing these indications to the operating field, with an increased risk of being inaccurate or of carrying out a bad work.

Despite the existence of augmented reality devices, it is not possible to use them, since the correlation cannot be made between the actual view of the patient's mouth and the information from the augmented reality. Even if the information from augmented reality would appear on the remote display screen, the display on the remote screen would never be seen by the user in real time and his gesture would not be positioned accurately in his working field.

The remote display screen has also an influence on the quality of the optical imprint: the user never has a real and direct correlation that permits him to know whether the taking of the imprint is complete or not. There is also as risk that he moves the intraoral camera in an uncontrolled way at each eye movement, whence the results are uncertain.

The display on a remote screen of the modeled representation of the organs of the mouth (for example representation of what should be the teeth and gums at the end of the work, once the dental prosthesis has been placed) cannot occur at the same time as the live visualization of the same organs. This also applies to all the information from software related to the augmented reality displayed on the remote screen.

The user's eyes do not necessarily see all areas accessible for the intraoral camera, which makes it difficult, even impossible to estimate what has been measured. This drawback is especially true if the intraoral camera is a device such as an optical imprint holder, which is bulky and hides a significant portion of the patient's mouth.

Since the user cannot see the patient's mouth and the result of his work together in real time in a single repository, his gesture may not be secure.

SUMMARY OF THE INVENTION

The aim of the present invention is to cope with the above-mentioned drawbacks.

The invention relates to a device for visualizing the interior of a patient's mouth, the device comprising a camera adapted for taking an optical imprint of organs arranged in the mouth, wherein it comprises augmented reality glasses having, on the one hand, an optical glass through which a user of the glasses can see the interior of the mouth and, on the other hand, a visualization camera filming what the user sees through the optical glass, first images corresponding to those taken by the visualization camera being correlated with second images corresponding to those taken by the camera for taking an optical imprint, whereby the second image can be projected onto the optical glass.

Thus, the invention provides a visualization device, which permits to bring together in the same field of vision (the optical glass, and thus the patient's mouth) in a correlated way, the direct visualization of the interior of the patient's mouth and the second images that correspond to those taken by the camera for taking an optical imprint. These second images can be both the images taken by the camera for taking an optical imprint and the images from a computer modeling of the images taken by this camera.

If the user wishes so, he can thus follow the evolution of his work (for example, establishing a diagnosis or making an imprint) without taking his eyes off the patient's mouth.

Thanks to the presence of a single field of vision, there is no longer any risk for the user to make adverse, inaccurate and uncontrolled movements with his hands, which is an even more significant advantage when he works in three-dimensional dynamic measurement.

By eliminating the diversion of his eyes from the patient's mouth, there is no longer any risk for the user to cause an injury to the patient. The gestures by the user and the information that helps him carrying out his work are permanently in the same field of vision.

Due to the absence of movement of the eyes (namely at very high rhythm), the user is clearly less tired by the use of the device according to the present invention.

The correlation between the actual view and the modeled view permits the user to be able to use any method for taking an optical imprint, whether it is or not a method using a structured active light.

The device according to the invention permits to have a three-dimensional stereoscopic natural restitution without being obliged to use three-dimensional screens that are always expensive and often inefficient.

The camera for taking an optical imprint is by definition a camera that can take an imprint in a contactless way.

The camera for taking an optical imprint can be a camera carried by the augmented reality glasses, an intraoral camera (movable manually), or an optical imprint holder. The camera for taking an optical can be an intraoral optical imprint holder system (both a relatively bulky optical imprint holder system, which includes projecting and reading devices and uses either holographic interferometry or optical fibers carrying moiré images, and an optical imprint holder system, which uses the principle of the stereoscopy in incoherent light and which includes an optoelectronic support provided with several cameras scanning at one time the whole field the imprint of which must be taken).

The camera for taking an optical imprint can use photonic radiations (ranging from deep blue to X-rays) or ultrasound radiations. It can use (or not) coherent radiations.

This camera can also be associated with a stereoscopic interferometry device or a projector projecting a structured light (a point, a line, a grid . . . ) on an organ of the mouth (typically the teeth or the gum).

It can be associated with a system for measuring and analyzing the shapes of the organs, the function of the system being making a precise recording of the shapes and colors of the organs. In the case where the system for measuring and analyzing is an active and/or structured light projector, the camera for taking an optical imprint possesses at least two (combined or separate) channels, one for projecting and the other for picking up the image. The projection channel (the projection can occur by LED, OLED, halogen, plasma or laser) projects onto an organ a structured radiation, which is deformed depending on the shape of the surface of the organ, this deformation being transmitted to a sensor via the image pickup channel. This permits the camera for taking an optical imprint, by a comparison of the characteristics of the projected (or stored) light with the distorted light that reaches the sensor, to know the shape and the dimensions of each organ object of the analysis. The camera for taking an optical imprint can also be associated with a system for measuring and analyzing the shapes of the organs of the mouth, which uses single or multi-camera telemetric or stereoscopic methods (this measuring system has the advantage of being simple, but the software being used is more complex). The camera for taking an optical imprint can also be associated with a system for measuring and analyzing the shapes of the organs of the mouth formed by a peripheral instrument such as a radiology device, an optical coherence tomography device (OCT) or an ultrasonic radiation device (provided these instruments provide metric information about the area being examined).

The device according to the invention also permits the user to know what is happening in the patient's mouth despite the presence of the camera for taking an optical imprint (namely in the case where this camera is an optical imprint holder).

The device according to the invention can comprise several cameras for taking an optical imprint. Each of the cameras for taking an optical imprint can be associated with a system for measuring and analyzing.

In order to optimize the analysis and taking of an imprint, the device according to the invention can be associated with a lighting system that can operate with or without structured light.

This lighting system can project from the outside of the mouth or be fastened to the camera for taking an optical imprint.

The lighting system being used, depending on the type of lighting, can cause additional information on the organs being measured to appear as augmented reality information. Thus, according to the wave lengths of the lighting, it is possible to determine and/or find some dental anatomical elements and to indicate them on the optical glass.

The lighting system can also be adapted for projecting some information, without having to use augmented reality. This can be for example a projected code (such as a red circle) indicating where the accurate reading of the camera for taking an optical imprint is located. The lighting system can change the color or the shape of the information depending on the quality of the acquired data.

The augmented reality glasses comprise at least one optical glass (generally two) and at least one visualization camera. The presence of several visualization cameras on the augmented reality glasses permits namely to re-adjust in real-time the modeling from the reading by the camera for taking an optical imprint.

The visualization camera is not necessarily a three-dimensional camera: it can also be a two-dimensional camera or a two-and-a-half-dimensional camera. The device according to the invention can correlate two-dimensional images taken by a visualization camera with three-dimensional images taken by the camera for taking imprints. In the case where the camera is a two-and-a-half-dimensional camera or a three-dimensional camera (the glasses having a spatial vision), the correlation is very accurate and the indications occur on portions of the organs read in three dimensions (some augmented reality glasses have dedicated specific optical glasses making results possible).

The optical glass through which the user has a direct view of the mouth is also the place where the first images corresponding to those taken by the visualization camera can be projected, the second images corresponding to those taken by the camera for taking an optical imprint, and eventual additional information that can be associated with the augmented reality and with external peripheral instruments (for example a viewable sign, such as a variation of intensity, of color or of contrast).

The user can see the evolution of his work. For example, he can know if the taking of an optical imprint is complete and accurate or whether he must intervene again to complete it, whereby this indication can occur through a gradual substitution of the direct vision through the optical glass by the second images representing the imprint being taken.

The additional information can be projected onto the optical glass (in real-time or delayed, at the user's option) can be directly correlated on the optical glass, as the augmented reality permits. This additional information can proceed from peripheral instruments such as X-ray, optical coherence tomography (OCT) or ultrasonic radiation devices. The use of the augmented reality for the additional information permits to guide the user (namely if organs have not been taken in the imprint), to show him sub-gingival information by using previously stored radiological information, to draw his attention during a surgical procedure if the latter is not executed perfectly (for example, by indicating undercut areas or lack of parallelism between the pillars of a bridge before a final taking of an imprint). It is also possible to associate the dynamic movements during the carrying out of coronoplasty or occlusal analyses, to visualize the effect of the planned positioning of brackets on the teeth, to know the distribution of the dental tissues during the preparation of cavities for receiving a cover or crown (for example, the proximity of the pulp).

The augmented reality glasses being used can for example be "Google Glass", "Vuzix smart Glass", "K-Glass" or "video-projection Epson" glasses.

A three-dimensional tracking system can be associated with the augmented reality glasses, so that the user can follow the progress of his work, and in particular the progress of his optical measurement action directly in correspondence on the organs of the mouth.

The device according to the invention can also comprise a central data processing unit that namely permits to correlate the first images corresponding to those taken by the visualization camera with the second images corresponding to those taken by the camera for taking an optical imprint.

Typically, the central unit is suitable for converting analog data and/or digital data and for managing data (digitizing the various images taken by the camera for taking an optical imprint and the visualization camera, measuring different information contained in these images, processing these images by a computer, correlating them, gathering them on the optical glass . . . ). The central unit also permits to add additional information about the patient, in order to inform and assist the user (for example, the indication of the organs that have been measured).

The central unit permits to bring together in the same object the first images with the second images. These first and second images are taken from the same area of work, but have different information. Depending on the circumstances, the central unit substitutes or superimposes the second images on the first images.

The correlation followed by a substitution between the two types of images of the same area of work results into a gradual enrichment of the direct view by the user with the second digitized and processed images. For example, each organ located in the mouth has visual peculiarities, which a cloud of points is associated with. The central unit, on the one hand, finds the same cloud of points on the first and the second images (generally, as regards the second images, as these second images are being taken) and, on the other hand, correlates the two types of images by displaying the second images that are much more accurate than the first images. This display of correlation can be performed in a particular color. The user thus sees the measured area (for example red colored) directly and gradually appear on the optical glass, this even if this area is hidden by the camera for taking an optical imprint (namely in the case where the camera is an optical imprint holder), the second images being taken by the camera precisely imprinting optical.

The central unit can also have other functions, such as permitting to calculate, for an organ, a spatial three-dimensional cloud of points, to add thereto the duration of the movements of the organ (the fourth dimension) and its color shade (fifth dimension).

The central unit can comprise an image processing software provided with several algorithms. Thus, an image flow proceeding from one or two two-dimensional cameras is processed in real time, so as to produce a first three-dimensional reconstruction in real time viewable by the user as he moves the camera for taking an optical imprint around the organ. The overall scheme of three-dimensional reconstruction in real time and the organization of the data vary depending on the number of cameras being used: either two two-dimensional image flows, each of these image flows proceeding from a two-dimensional camera, or a two-dimensional image flow proceeding from a single two-dimensional camera associated with an acceleration data flow proceeding from an accelerometer. Each newly acquired image is processed by a algorithm for searching an optical trace by calculating points of interest and by matching through the images. From the correspondence, a sequencing algorithm in real time then updates the sequencing of the video stream for a better temporal performance. A parallel estimation algorithm for the camera positions in space and the coordinates of the points in three dimensions then permits, thanks to the optical traces, to find the positions of the cameras at the time of acquisition and to generate the three-dimensional cloud of points projecting on the optical traces. The generated cloud of points is then interpolated by an interpolation algorithm, in order to obtain a denser cloud. An implicit interpolation function is also calculated, thanks to which a textured polygonalization of the surface to be reconstructed is obtained by a polygonalization and texture calculation algorithm. At this stage, it is possible to calculate quality indices of the final cloud of points and eventually to label certain points as invalid. The textured surface is displayed, eventually with suitable annotations to indicate the still invalid areas. This surface generated in real time is a representation of the reconstructed area at a scale factor. When the acquisition is completed, the scale factor is calculated by an algorithm for scaling the three-dimensional reconstruction. Finally, an algorithm for enhancing the spatial accuracy can be used on the three-dimensional model, in order to have the most accurate reconstruction possible. This enhancement algorithm recalculates a three-dimensional cloud of points, taking into consideration all the acquired views. The recalculated cloud is then interpolated by the interpolation algorithm, and finally an overall three-dimensional model is reconstructed by a "space carving" algorithm.

The device according to the invention can also be associated with peripheral instruments that provide additional information, such as X-ray, colorimetric, or mandibular movement information.

These peripheral instruments are preferably associated with the central unit, as well as the camera for taking an optical imprint and the visualization camera, so that the central unit can process the information provided by these peripheral instruments and project corresponding additional images on the optical glass of the augmented reality glasses.

A possible peripheral instrument is an extraoral camera adapted for taking part of the patient's face on a broad field. This camera is namely used for certain treatments, such as in orthodontics and implantology. With this extraoral camera can be associated the same functionalities as those described for the camera for taking an optical imprint or for the visualization camera (namely using or not structured light).

Another possible peripheral instrument is a two-dimensional camera adapted for taking images the information of which to be retrieved not necessarily needs to be very accurate, such as for example the color shade of the teeth, the presence of bleeding, damages to hard tissues (presence of caries), the presence of tumors or determined oral pathologies.

Other possible peripheral instruments are position-measuring instruments, such as accelerometers, gyroscopes and magnetometers. These position-measuring instruments can be carried by both the camera for taking an imprint and the reality glasses (for the visualization camera). These position-measuring instruments permit to measure the position of the tools that carry them and to facilitate the correlation of the images being taken. They can also compensate for an eventual failure of one of the sensors on either camera.

It is also possible to have, among the peripheral instruments, an articulator, pressure gauges and a digital occlusor. These instruments permit to visualize, analyze and incorporate into the images seen through the optical glass the movements of the patient's body, such as the mandibular movements or the response to the printing of some pathological images onto the gum.

Another possible peripheral instrument is a colorimeter or a spectrophotometer permitting to know the color of the teeth, whether in an absolute or in a relative manner with reference to known colors on stored shade guides.

It is also possible to have peripheral instruments permitting to know the patient's state of health during the operating action (for example, pressure and blood oxygenation, temperature of the body, the temperature of the lesion being examined, . . . ).

It is also possible to have dental peripheral instruments (for example radiological, ultrasonic, magnetic (MRI), terahertz . . . devices) permitting to take and record images of the organs of the mouth.

It is also possible to have peripheral instruments providing the user with additional information permitting to assist him during his work (this information can proceed from stored functions or intra or extramural software, for example by telemedicine).

It is also possible to have remote screens permitting to display information that the user sees on the optical glass and permitting assistants or students to follow the work being performed.

It is also possible to have a machine tool with numerical control that can produce a real part corresponding to the image seen by the user.

It is also possible to have a microphone (for example incorporated into a stem of the glasses) permitting the user to give orders to the central unit (for example for the appearance or disappearance of information on the optical glass).

It is also possible to have any other peripheral device permitting to communicate with the user, the assistants, the students and/or the central unit, or permitting to transmit and store the information, orders and data.

All the elements forming the device according to the invention can be connected to each other by cable, Bluetooth or Wifi (the latter two cases permitting to completely make free the gestures of the user).

The device according to the invention is simple in its manufacture, which makes it particularly resistant and inexpensive. It can be used in the dental offices and prosthesis laboratories. It permits the user to work in a fast, secure and comfortable way. It permits to make optical imprints in dentistry in optimal conditions. It also permits to optimize the therapeutic action by providing an accuracy in the range of one micron.

The device can be applied in a progressive way to any system for acquiring in three dimensions requiring a quick and precise handling obliging the user not to take his eyes off his field of work, analysis and/or measuring (as in medical, sports or industrial environments). It is thus possible to follow and inform the user in real (or almost real) time, while permitting him not to take his eyes off the scene and displaying information for him.

Further features and advantages of the present invention will become clear from the description of an embodiment of the device for visualizing the interior of a patient's mouth, this embodiment being given as a non-restrictive example and represented by the attached drawings.

BRIEF DESCRIPTION OF THE DRAWINGS

FIG. 20 is a photographic view of a representation of the taking of an imprint by means of the intraoral camera, which a representation of the lips and the cheek, displayed and visible through the optical glass of the augmented reality glasses, is associated with.

DETAILED DESCRIPTION OF THE DRAWINGS

The present figures represent different implementations of the device for visualizing 1 the interior of a mouth of a patient 2 according to the present invention, showing all the possibilities it offers in the daily practice of a user 3, for example a dental surgeon. This device finds a particular interest in the fields of dentistry.

Figure 1:
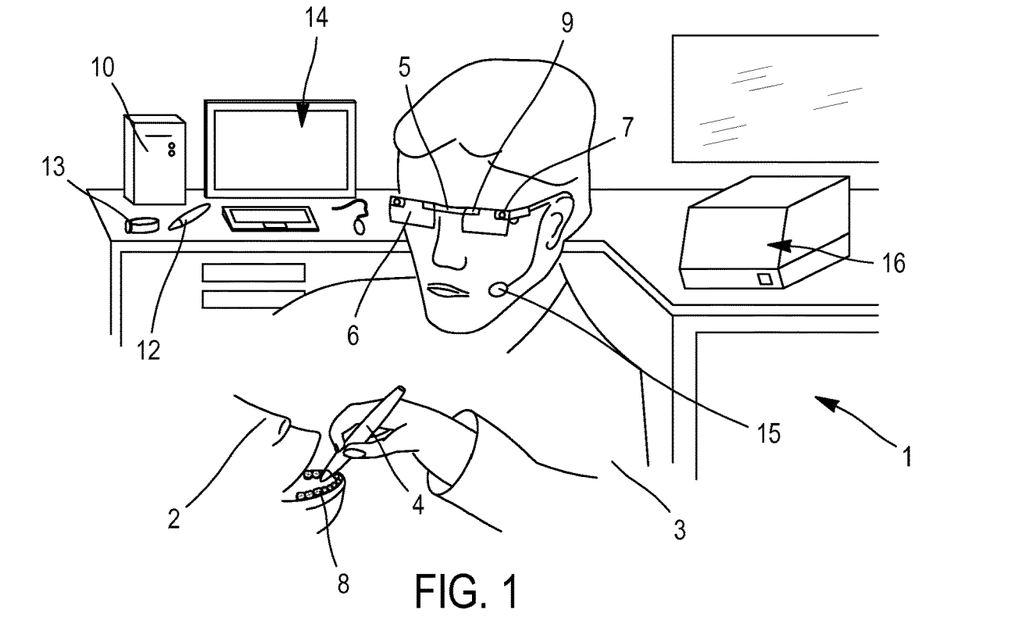
FIG. 1 is a schematic view of a representation of the device according to the present invention.

FIG. 1 shows elements of the visualization device 1, the visualization being enhanced thanks to the augmented reality process. The visualization device 1 permits the user 3 to never take his eyes off his operating field when carrying out his measurements or diagnostics.

The device 1 comprises a camera for taking an optical imprint 4. In this case, this camera for taking an optical imprint 4 is a manual intraoral camera permitting the user 3 (dentist or physician) to perform his measurements in three dimensions in the mouth or on the skin of his patient 2. Since this measurement is very accurate (a few microns) and very close to the teeth, the field depth is very low, which explains that the user 3 must proceed to a scanning of all the teeth, either by successive photographs (one shoot impression) or by filming in three dimensions (full motion). The camera for taking an optical imprint 4 could be an optical imprint holder, as described in U.S. Pat. No. 8,520,925, containing several cameras and permitting the user 3 to have the whole of the mouth at a time, without having to scan it.

The device 1 also comprises augmented reality glasses 5, which are carried by the user 3. These augmented reality glasses 5 comprise two optical glasses 6 and two stereoscopic visualization cameras 7. Therefore, it permits the user 3 to have a stereoscopic natural vision of the mouth 8 of the patient 2 and hence of the area he measures and he is examining. When the user 3 looks at this area of work, the visualization cameras 7 observe the same scene and proceed to a recording of information leading to creating a visualization cloud of points.

Since the head of the user 3 can move relative to the area being observed, to the augmented reality glasses 5 have been added, proximate the optical glasses 6, devices 9 facilitating the monitoring in space of the axis of observation of the user 3 (accelerometer/gyroscope/magnetometer in three dimensions). Although it is not compulsory, this addition largely facilitates the work when the user 3 must move his eyes outside the area of work and then turn them back to the latter to continue his work.

The device 1 also comprises a central unit 10, which permits to process the images taken by the camera for taking an optical imprint 4 and those taken by the visualization camera 7.

The measures taken by the camera for taking an optical imprint 4 and those taken by the visualization camera 7 provide two files corresponding to the same area, but not with the same accuracy. These files can be simple electro-optical information or more sophisticated information, such as digital representations in the form of clouds of points, or even surface or volume modeling information. In any case, between these two files exist common values such as for example the points located in easily identifiable reference areas, such as the top of the cusps of the teeth or the bottom of their grooves. These common values (for example, the reference areas) permit the central unit 10 to merge and/or superpose the two files into a single one, while preserving their specificities.

The device 1 also comprises a lighting system 11, which can facilitate the reading in three dimensions of the teeth that have a very specular reflection. The illumination system 11 emits a specific light that can be an active and structured projection, such as for example the projection of grids, or other patterns. It would also be possible to use a camera for taking an optical imprint 4 that does not use structured light, but based on the principles of passive stereoscopy (AWS or the like), on the technique such as the time of flight, or on holographic techniques or their derivatives, such as optical coherence tomography (OCT).

The new visualization device 1 is fully universal and applicable to all forms of intraoral localized measurements. Unlike the architectural techniques traditionally used by augmented reality glasses, which are looking for specific points, the device 1 according to the invention uses a double optical imprint (the one from the camera for taking an optical imprint 4 and the one provided (at the same time or at a delayed time) by the visualization camera 7 carried by the augmented reality glasses 5) and enriches it and/or replaces it depending on their degree of accuracy.

The device 1 also comprises peripheral instruments, which are connected to the central unit 10 in order to be able to add to the measurement file, formed for example by a cloud of points, other additional files (other clouds of points), as X-ray or ultrasonic information or even extraoral volumetric information obtained using a two-dimensional camera 12 or a wide-field camera 13.

The user 3 can also export the data in order to display them on a remote screen 14 (also visible by his assistants) or on his central unit 10, the user 3 communicating using a microphone 15 independent from the glasses 5 or fastened on the latter. He can also use these data to make, on a machine tool 16, a quick machining during his work permitting to better understand the close environment during the preparation of the teeth that will receive the prosthesis. This machining can be done by subtraction (conventional machining by milling) or by addition (non-conventional machining such as laser fusion or stereo lithography).

It is obvious that in the case of using an optical imprint holder, the whole arch would be covered and the clinician would not be disturbed by the (continuous or pulsating) lighting being used.

Figure 2:
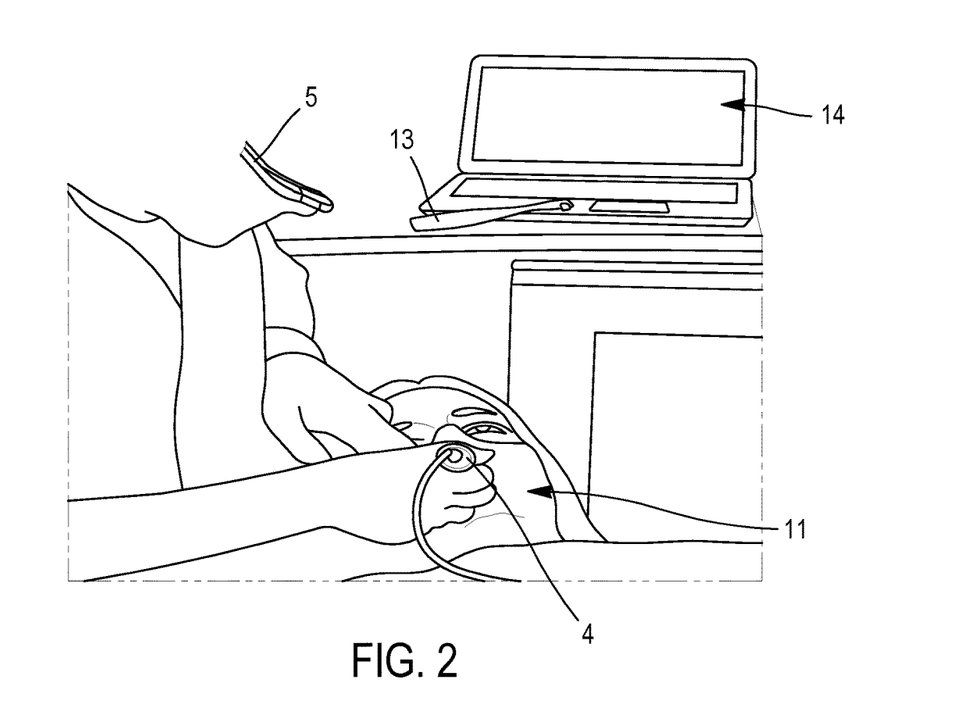
FIG. 2 is another schematic view of a representation of the device according to the present invention.

In FIG. 2 is shown that the invention, which comprises an intraoral camera for taking an imprint 4 in passive stereoscopy associated with a lighting system 11 projecting a specific light for measuring the teeth and gums (white light with a dominant of blues). The central unit 10, which is part of a laptop, is powerful and conventional. The same laptop has a screen 14 used by an assistant.

Figure 3:
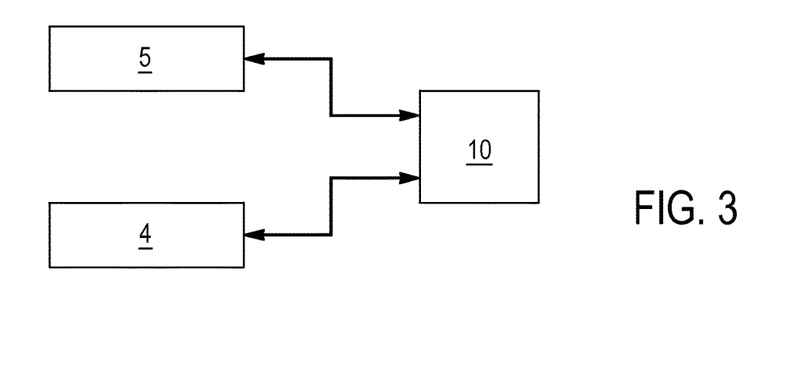
FIG. 3 is a schematic view of a representation of the organization of the essential elements of the device according to the present invention.

In FIG. 3 is shown the arrangement of the elements essential for the device 1 according to the invention: a camera for taking an optical imprint 4 (intraoral camera or optical imprint holder) for reading accurately the teeth, gums, skin . . . , augmented reality glasses 5 permitting the user 3 to see in one single field the operating field (in direct view) and the very accurate modeling performed by the camera for taking an optical imprint 4 (which is progressively displayed as it is being performed), and a central unit 10 which contains the stored programs and data.

Figure 4:
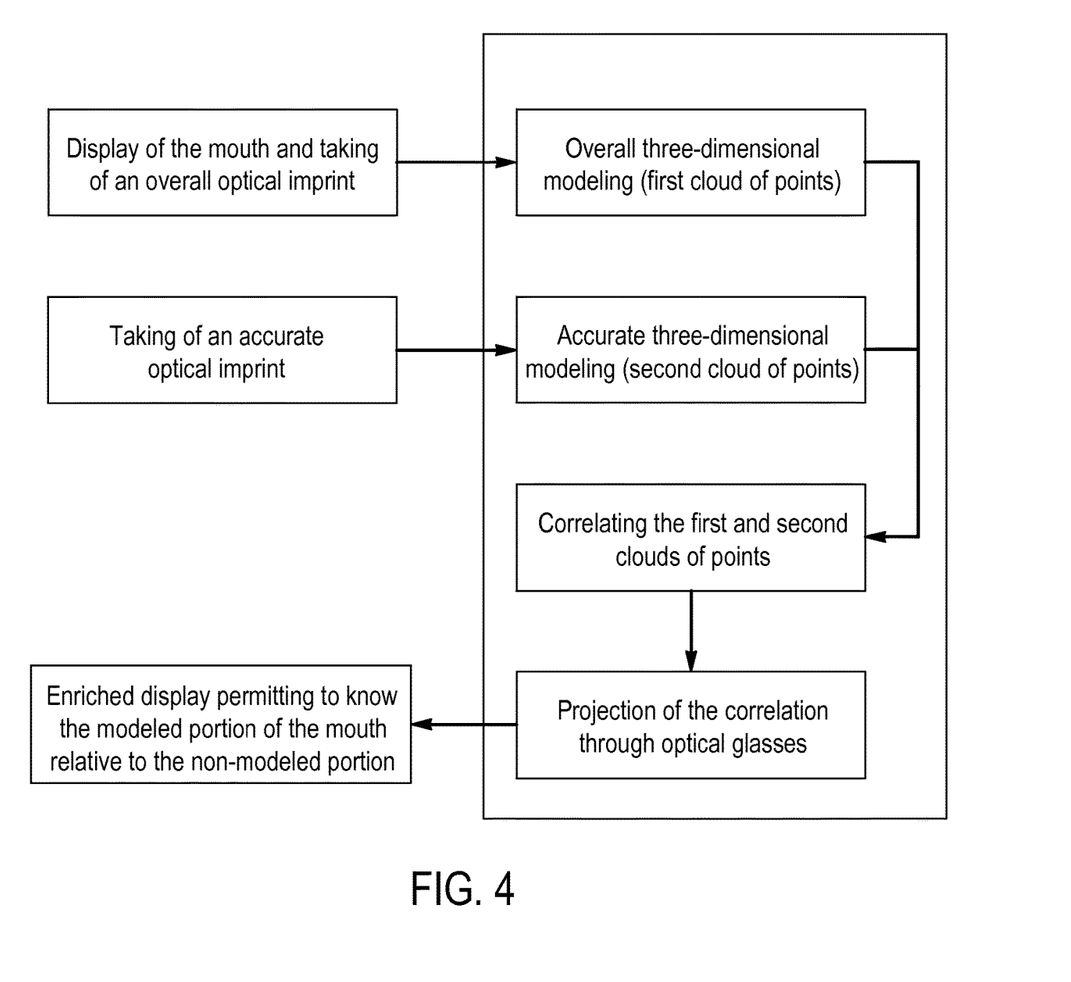
FIG. 4 is a schematic view of a representation of the steps of implementation of the device according to the present invention.

FIG. 4 illustrates the different steps of matching the view taken by the augmented reality glasses 5 with the view taken using the camera for taking an optical imprint 4.

The user 3 observes the field of work in the mouth 8 of his patient 2 directly through optical glasses 6 of his augmented reality glasses 5, the two visualization cameras 7 fastened to these glasses 5 performing a recording of a first cloud of points permitting the central unit 10 to model the entire surface in a general framework that is known and metric, but insufficiently accurate to make a dental prosthesis (here, the central unit 10 uses the principle of stereoscopy). The more visualization cameras 7 there are, the more the recording will be accurate, the higher the number of recorded points will be, and the more the correlation with the images from the camera for taking an optical imprint 4 will be accurate.

Once the visualization cameras 7 have finished the recording, the user 3 takes the camera for taking an optical imprint 4 in hand and performs an accurate scanning of the teeth, of the gums or eventually of the skin, leading to creating a second near cloud of points, but much more accurate than the one obtained using the visualization cameras 7, since the camera for taking an optical imprint 4 has a higher density and therefore greater accuracy than the visualization cameras 7. If the camera for taking an optical imprint 4 is an optical imprint holder as described in U.S. Pat. No. 8,520, 925, then the recording can occur without scanning.

During the reading by means of the camera for taking an optical imprint 4, the central unit 10 recognizes and correlates the two clouds of points obtained (the one from the two visualization cameras 7 and, as the scanning progresses, the one from the camera for taking an optical imprint 4). This double modeling appears on the optical glasses 6 of the augmented reality glasses 5. The user 6 must no longer follow his work on a remote screen 14. Thanks to the visualization device 1 he will see the measured areas and those that are not measured being built directly on the teeth of his patient 2.

Figure 5:
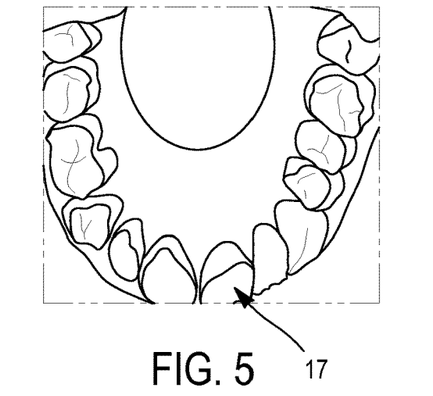
FIG. 5 is a photographic view of a dental arch through an optical glass of the device according to the present invention.
Figure 6:
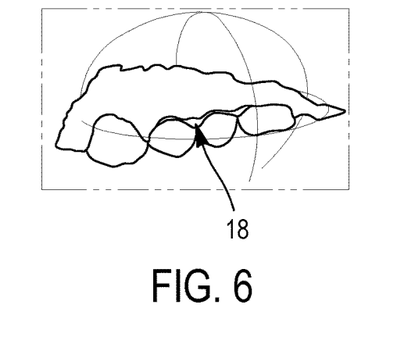
FIG. 6 is a photographic view of the modelling of the dental arch of FIG. 5 after taking of images by an intraoral camera for taking an optical imprint of the device according to the present invention.
Figure 7:
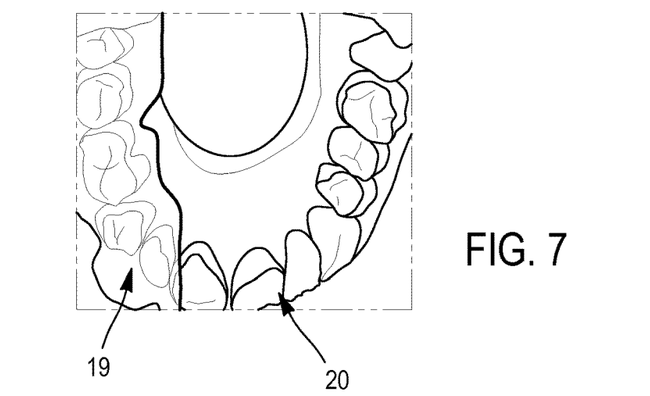
FIG. 7 is a photographic view, through the optical glass, of the dental arch of FIG. 5, the portion of the arcade the imprint of which has been taken being replaced by the accurate modeling of that portion of the arcade.

FIGS. 5 to 7 illustrate more specifically these steps. FIG. 5 represents a dental arch 17, which is seen by the user 3 and by the visualization cameras 7, the latter performing the recording of the first cloud of points of the arch 17. The corresponding modeling is here in three dimensions, two-dimensional or two-and-a-half-dimensional views would be enough. Once the recording of the first cloud of points is completed, the user 3 takes the camera for taking an optical imprint 4 and starts making an accurate recording of the organs (teeth, gums, skin) and obtains an accurate modeling 18 in a three-dimensional vestibular view of a portion of the arch 17 (FIG. 6). The central unit 10 causes the two clouds of points to correspond in the optical glasses 6 carried by the user 3. The latter sees, as his work with the camera for taking an optical imprint 4 progresses, the accurate modeling 18 being replaced or superimposed on the entire arch 17, which has to be measured accurately. As illustrated in FIG. 7, the direct vision of the arch 17 is thus increased by the indication of the measured areas 19 (corresponding to the precise modeling 18), compared to those that are not measured 20, which permits the user to monitor the progress of his work.

Thanks to augmented reality, and depending on the quality of information gathered by the camera for taking an optical imprint 4, it is possible to superimpose different additional information. Thus, the quality of the accuracy of the picture taken by the camera for taking an optical imprint 4 can be associated with additional information (for example, red color if the quality is insufficient, green color if it is perfect), the user 3 maintaining the choice of whether continuing his scanning with the camera 4 or returning to an area of insufficient quality. Likewise, additional information can be particular signs (for example, an arrow) indicating a particular area or reminding a particular action to be performed.

Figure 8:
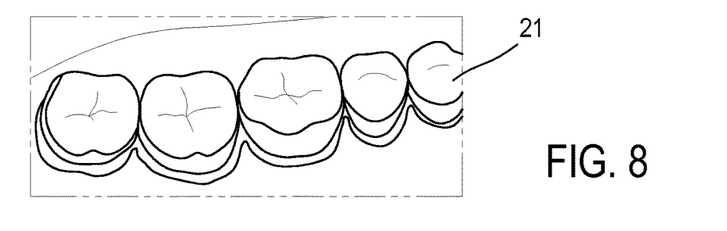
FIG. 8 is a photographic view of a series of teeth through an optical glass.
Figure 9:
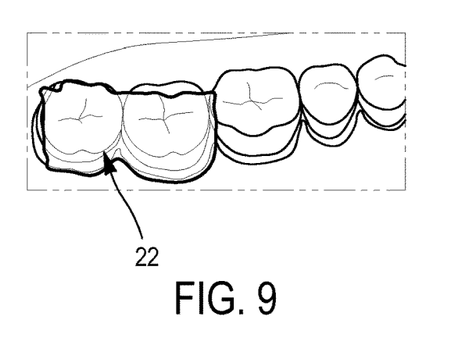
FIG. 9 is a photographic view representing an automatic matching by software of the homologous points of the view of FIG. 8 with a cloud of points.
Figure 10:
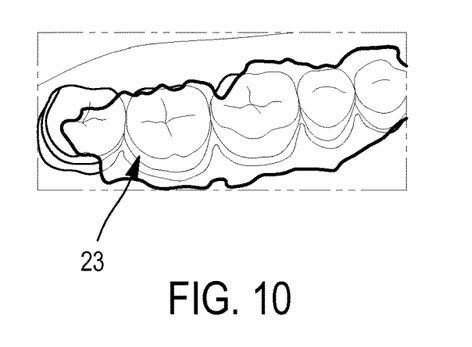
FIG. 10 is a photographic view representing an automatic matching by software of the homologous points of the view of FIG. 8 with a wired modeling.

FIGS. 8, 9 and 10 permit to see correlation operations. FIG. 8 shows a real model 21. FIG. 9 shows a correlation, on the last two molars, of a cloud of points 22 from a camera for taking an optical imprint 4. FIG. 10 shows a correlation from a wired modeling 23.

Thanks to the invention, the user 3 has a very accurate optical imprint (provided by the camera for taking an optical imprint 4), correlated and enriching the inaccurate view provided by the visualization cameras 7. The user 3 thus sees a relatively inaccurate real object, while he can work on a new virtual environment, in a fully transparent way, by taking advantage of the high accuracy provided by the camera for taking an optical imprint 4.

Figure 11:
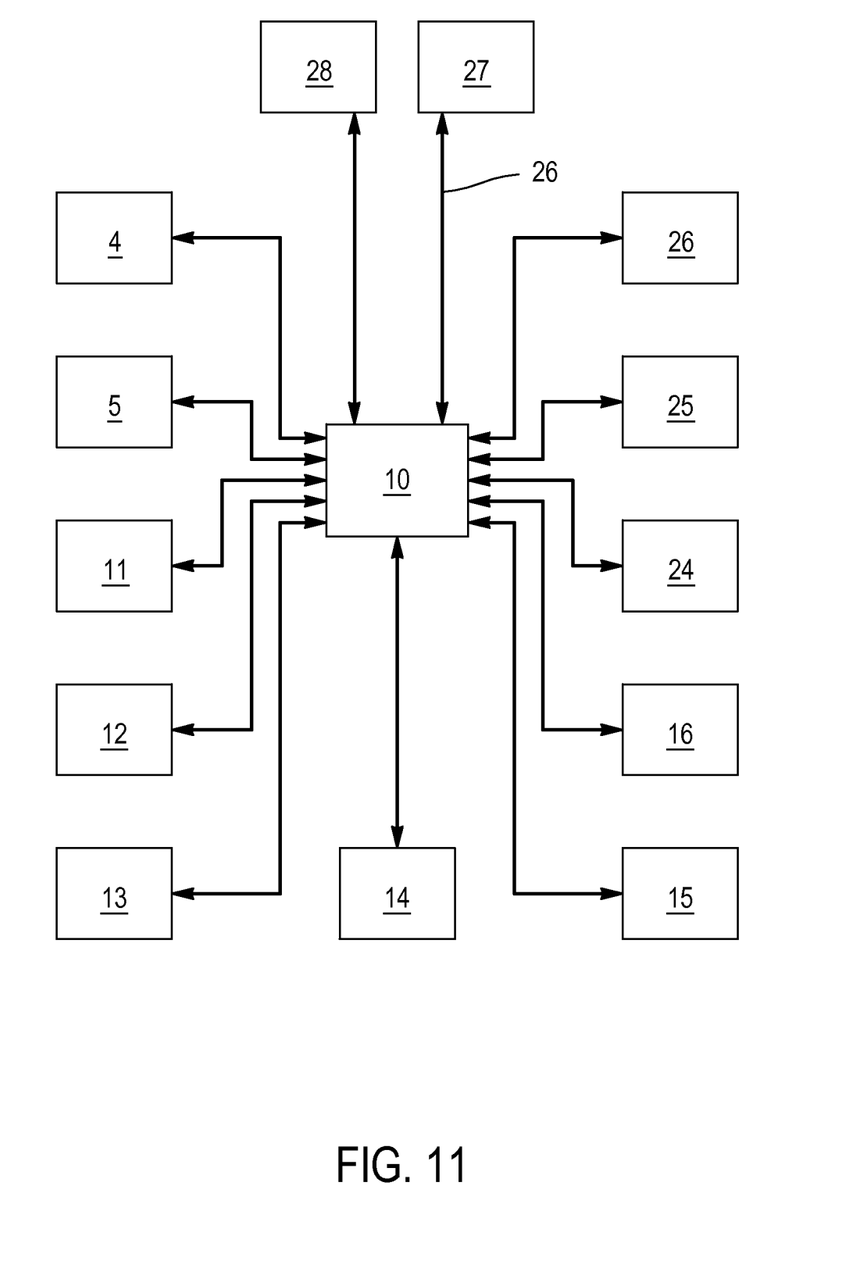
FIG. 11 is a schematic view of a representation similar to that of FIG. 3, but representing also elements forming accessories of the device according to the present invention.

FIG. 11 shows part of the possibilities provided by the peripheral instruments associated with the device 1 of the present invention in the field of dentistry.

All the additional information from the peripheral instruments (external cameras 12, 13, sensors 24 for the dynamic movement data, colorimeters 25 permitting to detect the colors in the mouth 8, medical sensors 26 analyzing the physiological state of the patient 2, instruments 27 analyzing radiological data arriving in real time or delayed in time, instruments 28 permitting the connection of the external data arriving through telemedicine or stored in the central unit 10) are plotted on an accurate modeling obtained in high definition by the camera for taking an optical imprint 4 correlated on the direct vision, which is less accurate, but directly observed by the user 3 in his field of work.

The gesture of the user 3 will be the more free and his direct vision as the connections 29 between the various components of the device 1 will occur by means of a long cable or wireless (WiFi, Bluetooth . . . ). If the connections 29 are made by cables, they will preferably be made by means of a self-powered USB connection. Advantageously, the connections 29 occur wireless.

The user 3 can receive static and dynamic additional information by following the movements in time of the changes in the view enriched by the camera for taking an optical imprint 4 and displayed in augmented reality through the optical glasses 6.

Figure 12:
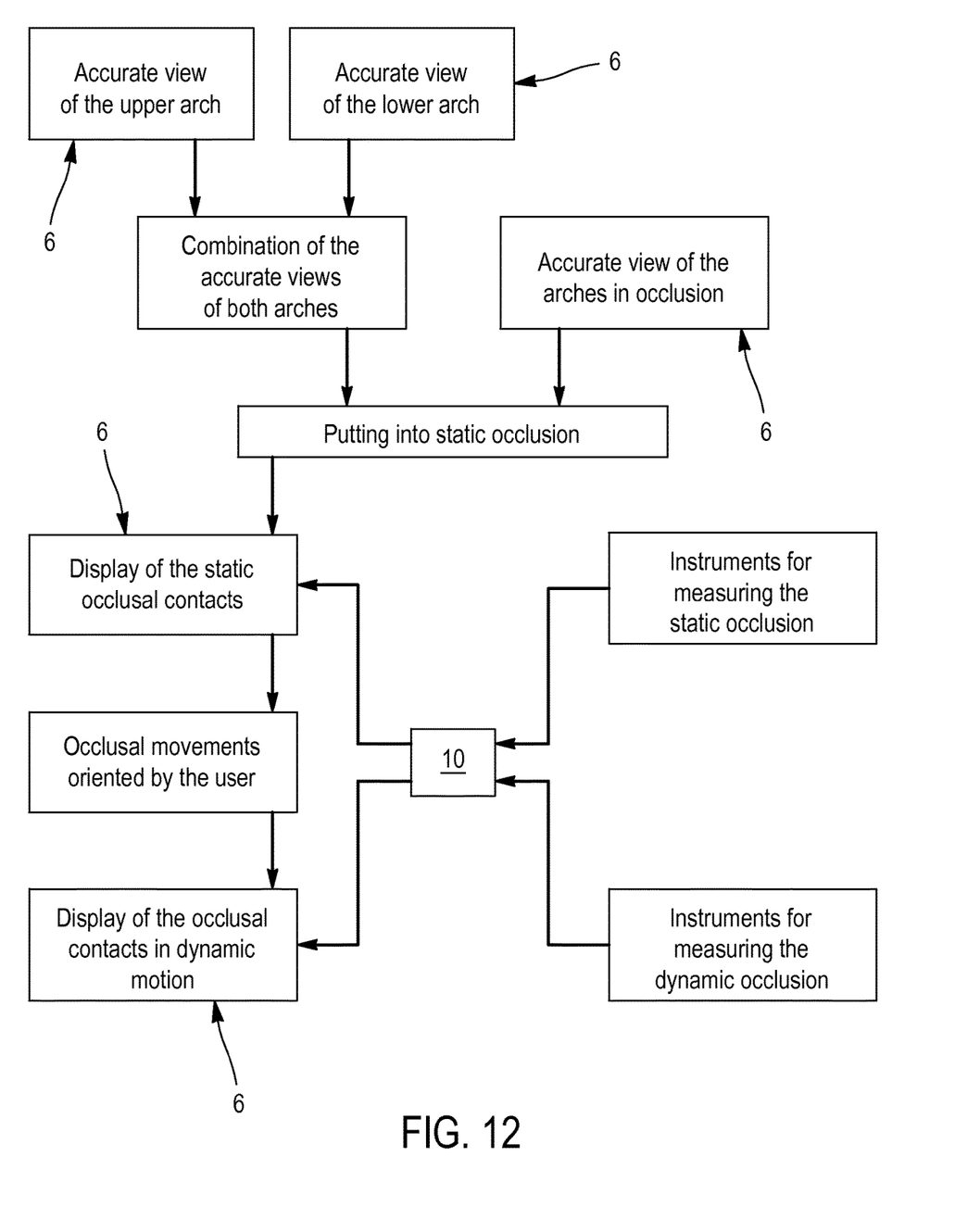
FIG. 12 is a schematic view of a representation of the steps permitting to display and analyze the static and dynamic occlusion of a patient by the device according to the present invention.

FIG. 12 illustrates the processing of the dynamic additional information, namely for the movements of occlusion (the occlusal contacts being areas where the upper teeth and the lower teeth touch each other).

First, the user 3 makes an optical imprint of the upper jaw, then of the lower jaw of the patient 2 by means of the camera for taking an optical imprint 4 and can visualize each of the two views using the augmented reality glasses 5. Then the user 3 asks the patient 2 to bite down in therapeutic or convenience static clinical occlusion and takes again the camera for taking an optical imprint 4 in order to get an accurate vestibular optical imprint in occlusion and a visualization in occlusion. The latter replaces or is superposed onto the general view seen through the augmented reality glasses 5. The user 3 thus has a view with the patient's two arches according to the clinical principles of the clinical occlusion.

The user 3 can follow over time the movements of the model of mandible relative to the model of jaw, and can thus determine the occlusal contacts.

Figure 13:
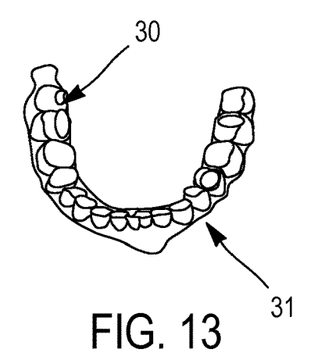
FIG. 13 is a photographic view of the areas into static contact determined by the device according to the present invention.

If the user 3 places between the teeth of the patient 2 means for measuring pressure and pressure surfaces (for example, pressure gauges) when the latter bites down, he can obtain a value of the pressure exerted and of the surface involved at each level of the occlusal contacts. FIG. 13 shows a view of these occlusal contacts 30 projected on a modeled arch 31. These values can also be measured very accurately (to within a few microns) by the camera for taking an optical imprint 4 when the patient 2 bites down.

Figure 14:
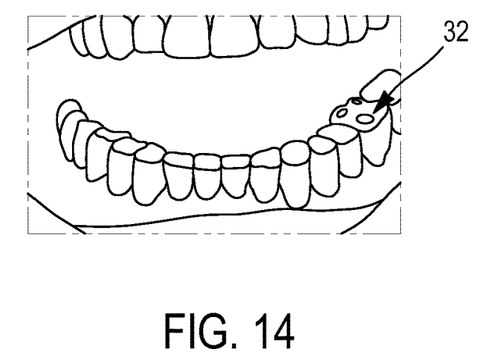
FIG. 14 is a photographic view of the areas into dynamic contact determined by the device according to the present invention.

FIG. 14 illustrates a representation on an optical glass 6 of the so-called premature occlusal contacts 32 obtained after the user 3 has requested the patient 2 to move his mandible according to occlusal movements. Here too, the user 3 of the visualization device 1 can follow these movements and the occurring of these contacts 32 directly in the mouth of the patient 2 (contacts applied against the natural teeth), without having to take his eyes off the field of work.

Figure 15:
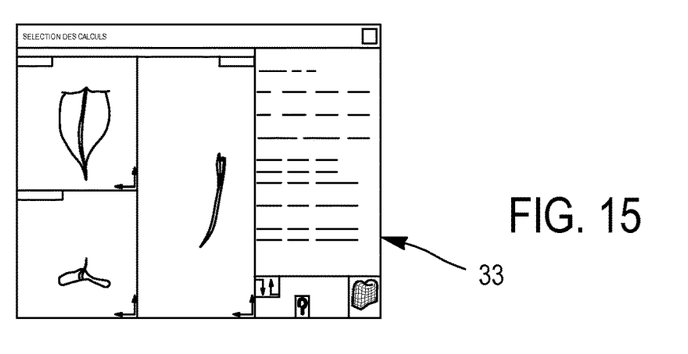
FIG. 15 is a photographic view of an example of representation of what is projected onto the optical glass in order to permit to follow in real-time the dynamic movements of the occlusion of the patient.

If the user 3 uses a mandibular analysis device 33 as shown in FIG. 15, he can follow mandibular movements directly in the mouth of the patient 2 and have the occlusion paths, the previous and following determinants and the indication of the contacts that require eventual corrections. It is enough to index in real-time the time factor/movement on the cloud of points or on the modeling. Likewise, this time factor/movement can be used by the central unit 10 time-delayed if the user 3 wants to observe these movements later in order to analyze the evolution of the pathology or occlusal therapy (through a correlation taking as a reference common points such as grooves on the teeth or a structure of the gums).

Figure 16:
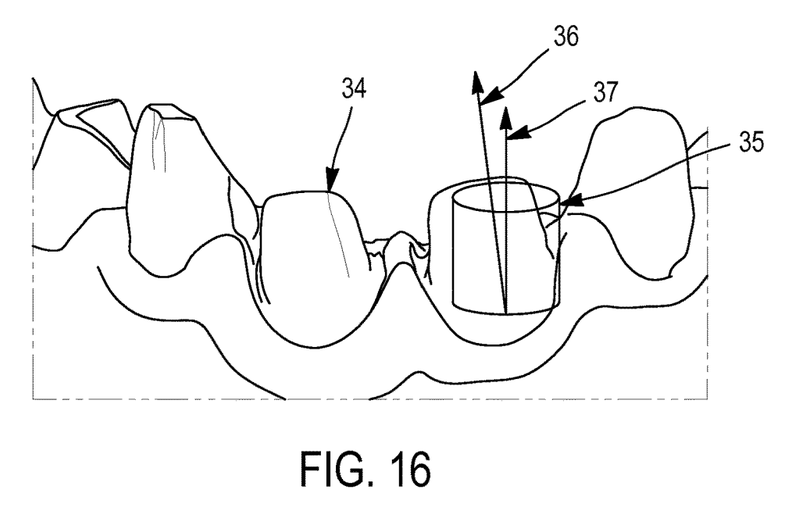
FIG. 16 is a photographic view, representing a taking of an imprint made by means of the intraoral camera for taking an imprint with, in superposition, the shape of the ideal preparation and the axis of insertion of the ideal preparation compared with the axis of insertion of the preparation carried out.

As illustrated in FIG. 16, the user 3 can see, during his work of preparation of a site for receiving a dental reconstruction 34, partial indications, which are directly applied on the precise modeling that coincides with the natural teeth of the patient 2. This information can be in different shapes (arrows, colored superposition for the undercuts, etc.). In particular, the user 3 can check, directly in the mouth 9 of the patient 2, if the criteria of form and space of the reconstruction are sufficiently met. The device 1 according to the invention permits to project on the teeth in preparation (through the optical glasses 6) much more accurately (thanks to the camera for taking an optical imprint 4), what should be a good preparation 35 or a good axis of parallelism 36 for a bridge or an implant relative to what this shaft is in real time during the work 37. This permits the user 3 to check his work as he carries it out (it is possible to have a visualization of the ideal underside surface with the dental parts not yet properly filed-down signaled by a specific visual mark, for example, highlighted in color).

Figure 17:
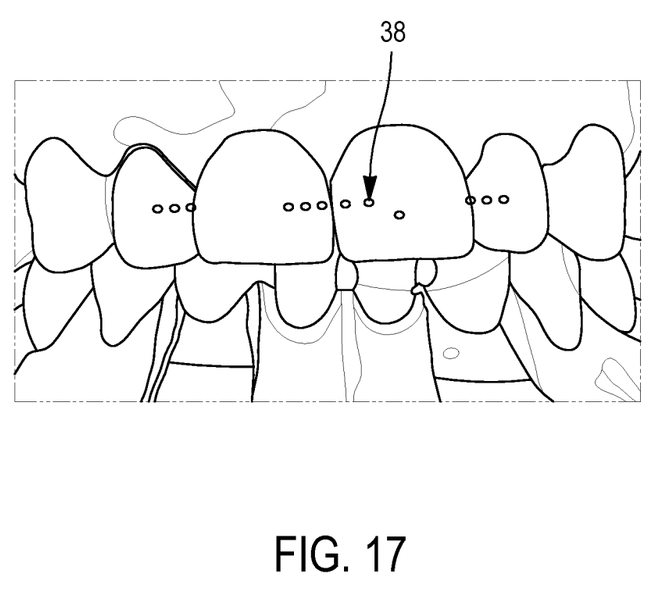
FIG. 17 shows a photographic view of a future prosthesis made using dental modeling software, seen in superposition on the taking of an imprint using the intraoral camera for taking an imprint.

As shown in FIG. 17, it is possible, after having carried out the tooth preparation, to project and visualize directly on the arch of the patient 2 the final modeling 38 of the prosthesis (before having made it). It is thus possible to build a modeling of the external surface of the prosthesis (in a surface or volume form) directly in the mouth 8 of the patient 2. It is even possible to act on the modeled shape of the prosthesis (based on the modeling from the augmented reality and the measurements made with the camera for taking an optical imprint 4) so that the actual prosthesis is perfectly adapted to the anatomy, the physiology and the aesthetics of the patient 2.

Figure 18:
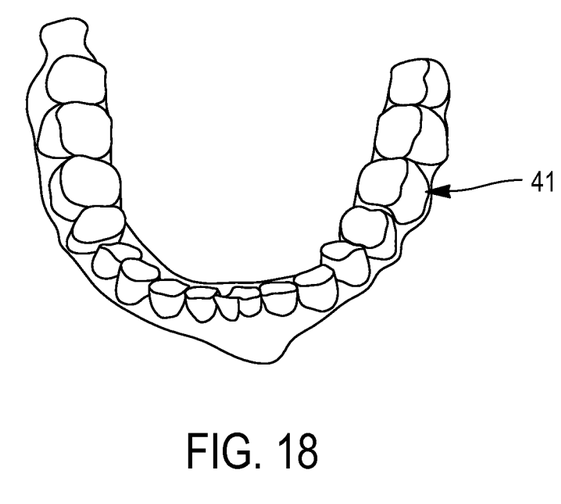
FIG. 18 is a photographic view of a representation in color of a complete arch made with the intraoral camera for taking an imprint.

As shown in FIG. 18, the user 3 can see directly on the area of work the correlation between the color chosen for a modeled prosthesis and the colors of organs of the mouth 8 of patient 2.

Figure 19:
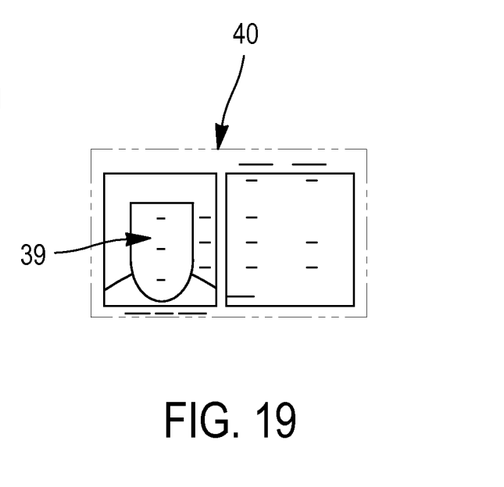
FIG. 19 is a photographic view of a representation of a screen visible through the optical glass of the augmented reality glasses, on which screen is displayed the colorimetric or spectrophotometric information depending on the areas involved.

More specifically, the steps of determining the color of the modeled prosthesis can be as follows. In a first step, a colorless external modeling of the prosthesis is carried out and projected onto the optical glasses 6 (if necessary, the user 3 corrects the modeled shape of the prosthesis namely depending on functional, aesthetic and therapeutic criteria). In a second step, the user 3 analyzes the color of the natural teeth (either manually using a shade guide, or using a device such as a colorimeter or spectro-photometer, or using an intraoral camera if the latter uses charge-couple devices (CCD) for color or for black and white with possibility of deriving the colors with a proper calibration), whereby the analysis can be done locally (by segmentation of the tooth 39, for example, by dividing it into a tooth collar, center and edge), as shown in FIG. 19, or generally from an average color obtained over the entire surface of the tooth. In a third step, the user 3 requests a projection of the modeled prosthesis associated with the chosen color. In a last step, using a virtual shade guide 40, such as that of FIG. 19, the user 3 can change the color of the modeled prosthesis either over the entire surface or in specific areas and see the consequences of these changes on the integration of the modeled prosthesis directly in the mouth 8 of patient 2 (thus, dark areas 41 to be changed are shown in FIG. 18) before launching the manufacture of the prosthesis.

Since the accuracy of the position of the colors is not as important as that required for creating the shape of the prosthesis, it may be possible that the accuracy of the visualization cameras 7 of the augmented reality glasses 5 is sufficient.

Figure 20:
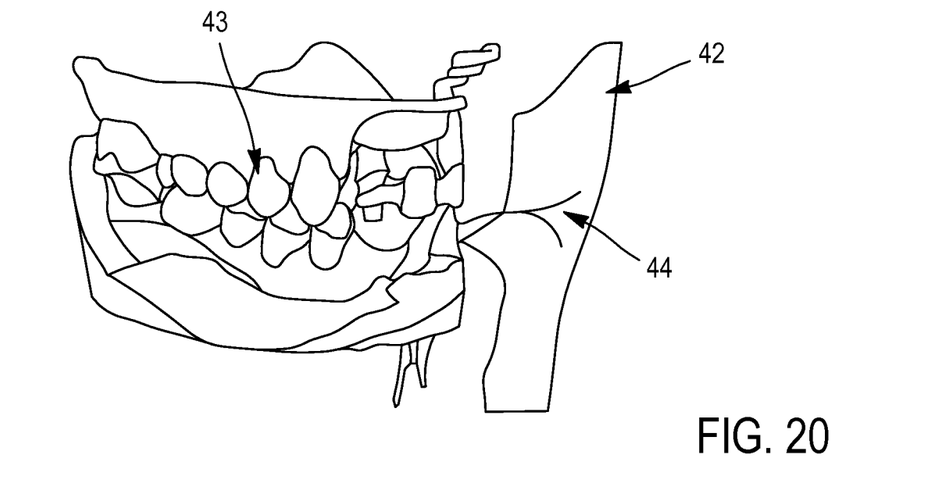

As illustrated in FIG. 20, the device 1 according to the present invention can comprise a wide-field camera (as an extraoral camera) permitting to take images of at least part of the face 42 of the patient 2. The central unit 10 can correlate these images of the face with all the above-described applications (for example, the modeling 43 of the organs and the prostheses), namely using general aesthetic components of the patient 2, such as the smile line, the Camper plane or the position of the corners of the mouth 44 (these components found by the central unit 10, can be displayed on the optical glasses 6 of the augmented reality glasses 5). Since the analysis of the position of general aesthetic components of the patient 2 does not require a high precision, it can be made from two-dimensional or two-and-a-half-dimensional images taken by a peripheral instrument that is simpler and cheaper than a camera for taking an optical imprint 4, such as an ordinary extraoral camera.

The user 3 can thus refine the aesthetics of the future prosthesis directly on the face of the patient 2, through the augmented reality glasses 5.

Finally, the central unit 10 can be connected to external information, thanks to a telemedicine network, and can thus control the display of information in real time on images that require some expertise (preparation) or a remote internal network for the assistants or the students in an educational center.

We claim:

1. A device for visualizing an interior of a mouth of a patient, said device comprising:
   augmented reality glasses being comprised of:

an optical glass having a field of work corresponding to an interior of the mouth; and a visualization camera having a visualization camera accuracy level and a visualization camera viewing area aligned with said field of work and determining a first images for visualization camera points and a first cloud of points corresponding to organs in said field of work; and an optical imprint camera having an optical imprint accuracy level and an optical imprint viewing area of said organs within said field of work so as to determine a plurality of second images for optical imprint points from said optical imprint viewing area and previous optical imprint viewing areas and a second cloud of points from said optical imprint viewing area and said previous optical imprint viewing areas corresponding to organs in said field of work, wherein said first images, correlates with said second images according to said first cloud of points being matched with said second cloud of points, wherein said optical imprint accuracy level is higher than said visualization camera accuracy level, the optical imprint points from said optical imprint viewing area being concurrent with said visualization camera points, said first cloud of points, and the second cloud of points from said optical imprint viewing area, and wherein said optical glass is further comprised of a double modeling in said field of work, said double modeling being comprised of a correlation of said visualization camera points, said first cloud of points, said second cloud of points from said optical imprint viewing area and said previous optical imprint viewing areas, and said optical imprint points from said optical imprint viewing area and said previous optical imprint viewing areas within said field of work.

2. The device for visualizing, according to claim 1, wherein said optical imprint camera is comprised of an intraoral camera.

3. The device for visualizing, according to claim 1, further comprising:
an illumination system positioned relative to said organs so as to illuminate said organs for said plurality of second images for said optical imprint points and the second cloud of points.

4. The device for visualizing, according to claim 1, wherein said correlation comprises a superposition of said second cloud of points from said optical imprint viewing area and said previous optical imprint viewing areas over said first cloud of points.

5. The device for visualizing, according to claim 1, wherein said correlation further comprises a replacement of a portion of said field of work corresponding to said first cloud of points with a portion of said field of work corresponding to said second cloud of points.

6. The device for visualizing, according to claim 1, further comprising:
a central unit in communication with said augmented reality glasses and said optical imprint camera so as to receive, store and process said first images, said first cloud of points, the second cloud of points, and the second images.

7. The device for visualizing, according to claim 6, wherein said central unit determines said correlation and said double modeling.

8. The device for visualizing, according to claim 6, wherein said double modeling is determined by additional information from said central unit.

9. The device for visualizing, according to claim 8, wherein said additional information relates to a patient and comprises data for making a dental prosthesis.

10. The device for visualizing, according to claim 8, further comprising:
first peripheral device connected to said central unit so as to capture said additional information.

11. The device for visualizing, according to claim 10, wherein said additional information is comprised of at least one of a group consisting of: static occlusion and mandibular movements, color of teeth, a shape of face, and physiological data.

12. The device for visualizing, according to claim 10, further comprising:
a second peripheral device connected to said central unit so as to capture further additional information.

13. The device for visualizing, according to claim 6, further comprising:
a microphone capturing control commands transmitted to said central unit.

14. The device for visualizing, according to claim 6, further comprising:
at least one measuring instrument being connected to said central unit so as to determine said double modeling and being selected from a group consisting of: an accelerometer, a gyroscope and a magnetometer.

\* \* \* \* \*